(12) United States Patent
Vasic et al.

(10) Patent No.: US 10,241,046 B2
(45) Date of Patent: Mar. 26, 2019

(54) IN-LINE DECAY-TIME SCANNER

(71) Applicant: SICPA HOLDING SA, Prilly (CH)

(72) Inventors: Milan Vasic, Geneva (CH); Nicola Duca, Monthey (CH)

(73) Assignee: SICPA HOLDING SA, Prilly (CH)

( * ) Notice: Subject to any disclaimer, the term of this patent is extended or adjusted under 35 U.S.C. 154(b) by 239 days.

(21) Appl. No.: 15/092,141

(22) Filed: Apr. 6, 2016

(65) Prior Publication Data

US 2016/0216207 A1    Jul. 28, 2016

Related U.S. Application Data

(63) Continuation of application No. 14/124,166, filed as application No. PCT/EP2012/002339 on Jun. 1, 2012, now Pat. No. 9,335,211.

(60) Provisional application No. 61/493,710, filed on Jun. 6, 2011.

(51) Int. Cl.
| | |
|---|---|
| *G01N 21/64* | (2006.01) |
| *G01J 1/58* | (2006.01) |
| *G07D 7/1205* | (2016.01) |

(52) U.S. Cl.
CPC ............ *G01N 21/6408* (2013.01); *G01J 1/58* (2013.01); *G07D 7/1205* (2017.05); *G01N 2201/062* (2013.01)

(58) Field of Classification Search
CPC ................................................ G01N 21/6408
See application file for complete search history.

(56) References Cited

U.S. PATENT DOCUMENTS

| | | | |
|---|---|---|---|
| 3,473,027 A | | 10/1969 | Freeman et al. |
| 3,628,034 A | * | 12/1971 | Ern ........................ G01D 5/347 |
| | | | 250/225 |
| 3,663,813 A | | 5/1972 | Shaw |

(Continued)

FOREIGN PATENT DOCUMENTS

| | | |
|---|---|---|
| CN | 101452592 | 6/2009 |
| CN | 100562898 | 11/2009 |
| EP | 0 066 854 | 12/1982 |

OTHER PUBLICATIONS

Larason T.C. and Bruce S.S. Metrologica, 35, Aug. 4, 1998, pp. 491-496.

(Continued)

*Primary Examiner* — David P Porta
*Assistant Examiner* — Djura Malevic
(74) *Attorney, Agent, or Firm* — Muncy, Geissler, Olds & Lowe, P.C.

(57) ABSTRACT

Scanner, method of scanning and system for scanning that allows detecting decay time characteristics of light emitted by a luminescent marking on an item which is transported, even at high speed, on a distribution/production line. The detection zone of the scanner's light sensor has a shape elongated along a path of the moving item, and the responsivity of the light sensor, within the wavelength range of the emitted luminescence light, is uniform over the detection zone. The drive current, or drive voltage, powering the excitation light source is adapted to deliver the intensity of the excitation light to the marking so that its light sensor can reliably measure the corresponding luminescence light response, and thus accurately determine a corresponding decay time value.

24 Claims, 7 Drawing Sheets

(56) References Cited

U.S. PATENT DOCUMENTS

| | | | |
|---|---|---|---|
| 4,451,521 A | 5/1984 | Kaule et al. | |
| 4,451,530 A | 5/1984 | Kaule et al. | |
| 4,452,843 A | 6/1984 | Kaule et al. | |
| 4,533,244 A | 8/1985 | Kaule et al. | |
| 4,598,205 A | 7/1986 | Kaule et al. | |
| 5,107,445 A * | 4/1992 | Jensen | G01K 11/3213 374/161 |
| 5,351,268 A | 9/1994 | Jensen et al. | |
| 5,459,323 A * | 10/1995 | Morgan | G01N 21/6408 250/458.1 |
| 5,636,015 A * | 6/1997 | Imura | G01J 3/4406 250/461.1 |
| 5,679,959 A * | 10/1997 | Nagase | G07D 7/00 250/458.1 |
| 6,020,959 A * | 2/2000 | Imura | G01J 3/02 250/461.1 |
| 6,264,107 B1 * | 7/2001 | Thomas, III | G06K 7/12 235/462.02 |
| 6,607,300 B1 * | 8/2003 | Kleinerman | G01K 11/20 250/483.1 |
| 6,762,840 B1 * | 7/2004 | Kimura | G01N 21/6428 250/458.1 |
| 6,777,704 B2 * | 8/2004 | Giering | G07D 7/1205 250/208.1 |
| 6,791,688 B2 * | 9/2004 | Lai | B01F 15/00207 250/458.1 |
| 6,996,252 B2 * | 2/2006 | Reed | G06T 1/0042 235/491 |
| 7,002,162 B1 * | 2/2006 | Fujimoto | G01N 21/6408 250/458.1 |
| 7,030,371 B2 * | 4/2006 | Vasic | G01N 21/6408 250/271 |
| 7,067,824 B2 * | 6/2006 | Muller | G06K 19/14 250/458.1 |
| 7,213,757 B2 * | 5/2007 | Jones | B41M 3/144 235/380 |
| 7,262,420 B1 * | 8/2007 | MacLeod | G07D 7/1205 250/458.1 |
| 7,427,030 B2 | 9/2008 | Jones et al. | |
| 7,595,473 B2 * | 9/2009 | Walt | G01J 3/02 250/205 |
| 7,675,620 B2 * | 3/2010 | Imura | G01N 21/251 356/300 |
| 7,750,802 B1 * | 7/2010 | Parish | G01N 21/64 250/370.01 |
| 7,928,408 B2 * | 4/2011 | Ok | G01J 3/02 250/458.1 |
| 8,263,948 B2 * | 9/2012 | Rapoport | G07D 7/1205 250/459.1 |
| 8,288,739 B2 * | 10/2012 | Imura | G01N 21/645 250/458.1 |
| 8,759,794 B2 * | 6/2014 | Rapoport | G07D 7/14 250/459.1 |
| 9,029,800 B2 * | 5/2015 | Kiesel | G01J 3/36 250/458.1 |
| 2002/0020818 A1 * | 2/2002 | Mitchell | G01N 21/6408 250/459.1 |
| 2002/0131618 A1 * | 9/2002 | Ahlers | G07D 7/1205 382/101 |
| 2002/0158212 A1 * | 10/2002 | French | B01L 3/50853 250/459.1 |
| 2003/0058441 A1 * | 3/2003 | Shakespeare | G01J 3/28 356/319 |
| 2006/0020403 A1 * | 1/2006 | Pusiol | G01F 1/716 702/45 |
| 2006/0204145 A1 * | 9/2006 | Vasic | G06K 7/10831 382/321 |
| 2007/0189595 A1 * | 8/2007 | Giering | G07D 7/122 382/137 |
| 2008/0137086 A1 * | 6/2008 | Imura | G01N 21/251 356/433 |
| 2008/0149855 A1 * | 6/2008 | Mehta | G01N 21/5911 250/492.1 |
| 2008/0186494 A1 * | 8/2008 | Kiesel | G01N 21/0303 356/440 |
| 2008/0230715 A1 * | 9/2008 | Nielsen | A61B 5/0059 250/458.1 |
| 2009/0086892 A1 * | 4/2009 | Boyden | A61B 5/415 378/44 |
| 2009/0086894 A1 * | 4/2009 | Boyden | A61B 6/00 378/44 |
| 2009/0086900 A1 * | 4/2009 | Boyden | G01N 23/223 378/45 |
| 2009/0086901 A1 * | 4/2009 | Boyden | A61B 5/415 378/45 |
| 2009/0086902 A1 * | 4/2009 | Boyden | A61B 5/415 378/45 |
| 2009/0108214 A1 * | 4/2009 | Shinoda | G01N 15/1425 250/492.1 |
| 2009/0152468 A1 * | 6/2009 | Allen | G01V 8/12 250/339.06 |
| 2009/0194705 A1 * | 8/2009 | Kiesel | G01N 21/645 250/458.1 |
| 2009/0266999 A1 * | 10/2009 | Krattiger | A61B 1/00096 250/459.1 |
| 2010/0108910 A1 * | 5/2010 | Morrell | G01N 15/0205 250/459.1 |
| 2010/0155577 A1 * | 6/2010 | Kiesel | G01N 15/1056 250/208.2 |
| 2010/0201988 A1 * | 8/2010 | Kiesel | G01N 21/05 356/419 |
| 2011/0052082 A1 * | 3/2011 | Parkov | G06K 9/2018 382/209 |
| 2011/0090485 A1 * | 4/2011 | Cronin | H01L 27/14601 356/71 |
| 2011/0121203 A1 * | 5/2011 | Rapoport | G07D 7/1205 250/459.1 |
| 2011/0241549 A1 * | 10/2011 | Wootton | F21S 8/006 315/117 |

OTHER PUBLICATIONS

International Preliminary Report on Patentability (IPRP) issued with respect to Application No. PCT/EP2012/002339.

\* cited by examiner

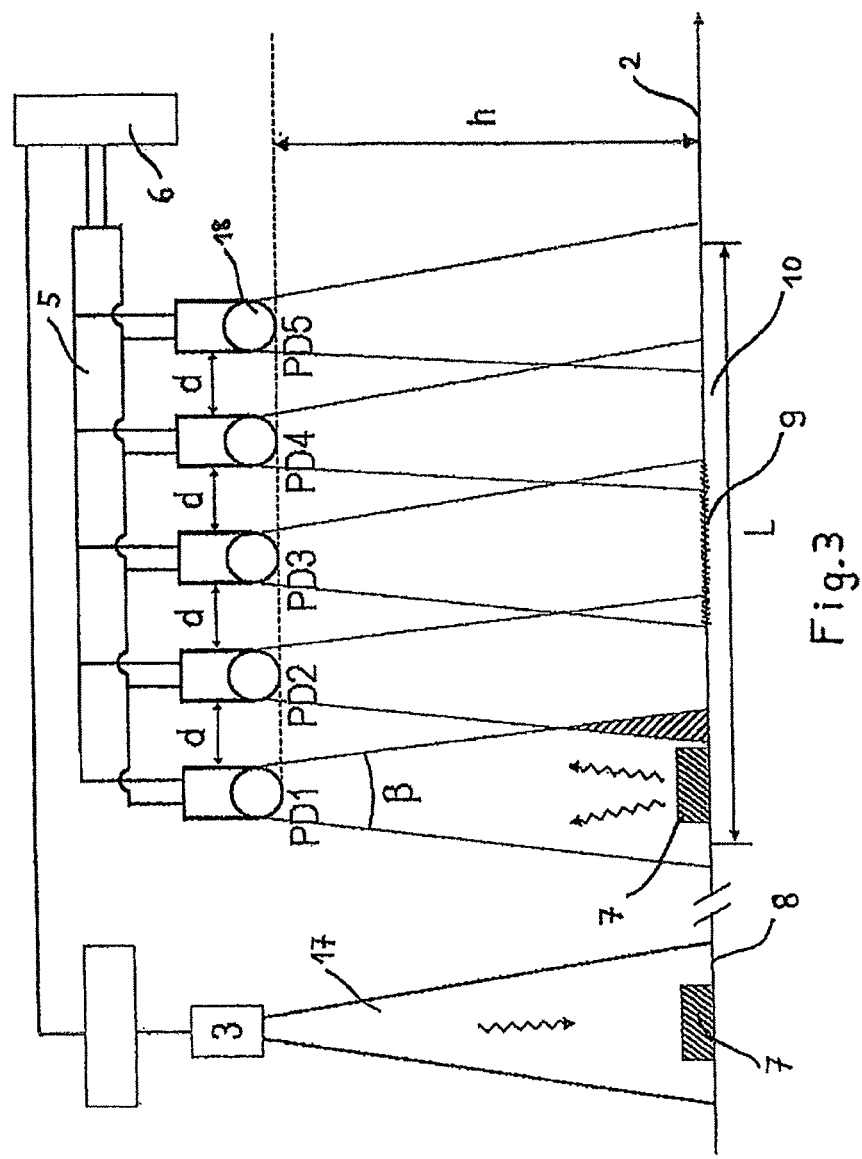

IN-LINE DECAY-TIME SCANNER

CROSS-REFERENCE TO RELATED APPLICATION

This application is a Continuation of U.S. application Ser. No. 14/124,166, which is a U.S. National Stage of International Application No. PCT/EP2012/002339 filed Jun. 1, 2012 claiming the benefit of U.S. Provisional Application No. 61/493,710 filed Jun. 6, 2011. The disclosures of U.S. application Ser. No. 14/124,166 and International Application No. PCT/EP2012/002339 are expressly incorporated by reference herein in their entireties.

TECHNICAL FIELD

The present invention relates to the technical field of optical devices for determining decay time characteristics of luminescence light emitted by a luminescent material. Particularly, the invention relates to optical devices such as optical scanners for authenticating an item marked with a luminescent material on the basis of the decay time characteristics of luminescence light emitted by said luminescent material.

BACKGROUND OF THE INVENTION

Luminescent materials are commonly used in security markings to be disposed on documents or articles, or in the bulk material of documents or articles, as an authenticity feature. A luminescent material typically converts energy of an exciting radiation of a given wavelength into emitted light having another wavelength. Luminescence emission used for authentication of a marking can lie in the spectrum range from UV light (200-400 nm), visible light (400-700 nm) or near to mid infrared light (700-2500 nm).

An "up-converter" material emits radiation at a shorter wavelength than that of the exciting radiation. By contrast, a "down-converter" material emits radiation at a longer wavelength than that of the exciting radiation. Most luminescent materials can be excited at more than one wavelength, and some luminescent materials can emit simultaneously at more than one wavelength.

Luminescence may be divided in: (i) phosphorescence, which relates to time-delayed radiation emission observable after the excitation radiation is removed (typically, with a decay lifetime from above about 1 µs to about 100 s), and (ii) fluorescence, which relates to prompt radiation emission upon excitation (typically, with a decay lifetime below 1 µs).

Thus, a luminescent material, upon illumination with excitation light within a first wavelength range, emits luminescence light within a second wavelength range, which may differ from or overlap with said first wavelength range, depending on the luminescent material used. A characteristic spectral property of a luminescent material such as its emission light intensity profile with time, or its characteristic decay time after excitation has stopped, for example, constitutes a signature of a presence of this very material and may thus be used as an authenticity feature for detecting genuineness or forgery of a luminescent marking.

Luminescent materials are classic ingredients of security inks or coatings. For example, the following patents disclose luminescent substances, which may include mixtures of pigments having distinct decay time properties, and security paper including such substances: EP 0 066 854 B1, U.S. Pat. Nos. 4,451,530, 4,452,843, 4,451,521. Processes and apparatuses for detecting luminescence light and authenticity of a marked item are also well known: see, for example, U.S. Pat. No. 4,598,205, or 4,533,244, which disclose sensing decay behavior of luminescence emissions. Luminescent coded symbols are known from U.S. Pat. No. 3,473,027, and an optical reader for luminescent codes is disclosed in U.S. Pat. No. 3,663,813. The patents U.S. Pat. No. 6,996,252 B2, U.S. Pat. No. 7,213,757 B2 and U.S. Pat. No. 7,427,030 B2 disclose using two luminescent materials, having distinct decay time properties, for authenticating an item.

Typically, a scanner according to the known art for detecting time-dependent luminescence light comprises a power source, or a connection to a power source, a light source (connected to the power source) for illuminating a luminescent material with excitation light, a light sensor for measuring an intensity of the luminescence light emitted by the luminescent material, and a control unit (processor) for controlling the power source, light source and light sensor to acquire and store an intensity profile of the emitted luminescence light, and calculating a decay time value from this intensity profile. A luminescence emission intensity profile (or intensity-versus-time curve) comprises successive emission intensity values $I(t_1), \ldots, I(t_n)$ from a luminescent material measured at the consecutive times $t_1, \ldots, t_n$, together forming a luminescence emission curve $I(t)$.

The light source in such scanner, depending on the part of the spectrum used for the detection of the luminescent material, may be an incandescent lamp, typically for wavelengths between about 400 nm to about 2500 nm, used with mechanical or opto-electronic devices for delivering pulsed light, or a flash lamp (e.g. a Xenon high-pressure flash lamp), or a laser or Light-Emitting-Diode (LED), emitting in the UV, visible or IR region, typically for wavelengths from about 250 nm to about 1 µm. The light source may be powered by a drive current (for a LED for example) or by a drive voltage (for a discharge lamp, for example).

The light sensors or photodetectors in such scanner may be photodiodes (single or arrays), phototransistor or photoresistance circuits, linear CMOS or CCD sensors, for example.

The scanner, in addition to its specific power module for supplying the scanner with power, may also comprise a communication module, which may be a radio module for wireless communication (over Wi-Fi, for example), a display module, e.g. a liquid crystal display LCD, or kinescope display, for displaying measured data or scanning parameters, and a controlling interface for inputting scan conditions, including control switches having multiple functions and an ON/OFF switch.

Most often, the time dependent intensity curve of luminescence emission light (i.e. intensity profile with time) from a luminescent material is modeled by an exponential law $I(t)=I_0 \exp(-\alpha[t-t_0])$, wherein time t is counted from initial time $t_0$ at which the excitation light illuminating said material is switched off. Thus, obtaining a value corresponding to the decay rate constant $\alpha$ characterizing the luminescent material necessitates measuring, after excitation has stopped, an emission intensity profile composed of successive emission intensity values $I(t_1), \ldots, I(t_n)$, over a time interval. The decay time value $\tau$ from the intensity profile $I(t)$ corresponds to $\alpha^{-1}$. In commercially available scanners, a pulsed light source illuminates the luminescent material with an excitation light of a given intensity, in a first wavelength range, during an excitation time interval. After the illumination has stopped, possibly with a time delay, the light sensor starts measuring successive values of the decaying luminescence light intensity in a second wavelength range over a measuring time interval, and the corresponding luminescence intensity profile is stored in a memory. The operation may be repeated so as to obtain more reliable average values. Usually, it is possible to set the excitation time interval and/or the time delay so as to avoid measuring values of luminescence intensity below a detection threshold value of the light sensor or above its saturation threshold value.

However, variants are also known. For example, U.S. Pat. No. 6,264,107 B1 discloses determining a decay time from the time required for the latent phosphorescence intensity to fall through two predetermined thresholds. This patent discloses a scanner comprising a flood LED (FLED) as a light source, i.e. a very intense light source. Such an intense light source is indeed necessary in this case for charging enough a tag comprising the luminescent material (phosphor) and preventing the problem of low signal response.

In another approach, U.S. Pat. No. 7,262,420 B1 discloses carrying out multiple illuminations with excitation light for obtaining a single decay time value: the light source is successively activated (during a same excitation time interval) and a single measure of luminescence intensity is performed after the illumination of the luminescent material with the excitation light source has been switched off, but each successive measurement is performed with a different time delay counted from the time at which excitation light is switched off. However, this method is time consuming, as it requires one illumination per measured intensity value. Moreover, in order to obtain more reliable results, this method requires repeated measurements corresponding to a same time delay.

In order to obtain a stronger luminescence signal, some scanners allow setting the excitation time interval, so as to "charge" enough the luminescent particles in the luminescent material (i.e. excite a great number of such luminescent particles to obtain more intense luminescence emission). Moreover, for a better accuracy of the determined decay time value, a plurality of valid intensity profiles are successively acquired (for example, about a hundred), these curves are then summed and an average curve is calculated. Increased accuracy is obtained if the resulting signal of the measured intensity is normalized and the normalized signal is used for calculating the decay time value. An intensity profile is valid if the intensity value of at least the first point of the intensity profile is above a detection threshold of the light sensor and below its saturation threshold (if said value is too low or too high, the excitation time is respectively increased or decreased). However, a problem arises in case where the excitation time interval is too short for allowing a reliable normalization of the luminescence intensity signal, particularly for luminescent materials including a mixture of luminescent particles of different types and of which decay time values are widely differing (for example, particles having the shortest decay time may not be detected by the scanner). Another problem arising with the use of variable excitation time is that the luminescent material is not excited under the same conditions for all the intensity profiles, and, in case of a material including a mixture of luminescent pigments having distinct decay time properties, this may cause confusion. For example, FIGS. 1A and 1B illustrate a case of normalized intensity profiles from a marking with an ink (luminescent material) including two types of luminescent pigments: pigments P1 and P2; in this example, the decay time value of pigments P1 is about 100 µs, and the decay time value of pigments P2 is about 500 µs. FIG. 1A shows an excitation curve (1) having a long excitation time interval of 100 µs, and a corresponding normalized luminescence intensity profile (P1+P2) for a luminescent ink material being a mixture of 50% of the first pigments P1 (having the shorter decay time, or higher decay rate) and 50% of the second pigments P2 (having the longer decay time, or lower decay rate). FIG. 1B corresponds to a luminescent ink including a mixture of 42% of the first pigments P1 and 58% of the second pigments P2. In this case, the excitation time has been adjusted to a shorter value of 10 µs, as shown on excitation curve (2). Although the concentrations of pigments in the mixtures of pigments P1 and P2 significantly differ from FIG. 1A to FIG. 1B, the normalized luminescence intensity profiles (P1+P2) are very similar and can hardly be distinguished. Thus, it is not always possible, or it may be difficult, to detect a difference between two mixtures on the basis of luminescence intensity profiles obtained by varying the excitation time. Although the above example relates to pigments having typical decay time values of about few hundreds of microseconds, a similar conclusion remains for pigments having much longer decay time values (few ms or more).

Another problem arising with said known decay time scanners is that they do not allow acquiring a luminescence intensity profile, and thus determining a corresponding decay time value, or decay time values and also concentrations in case of a mixture of different types of pigments, in case the luminescent material is moving past the scanner; particularly, in case the luminescent material moves fast past the scanner on a production/distribution line. For example, in case of items marked with a luminescent material and transported on a conveyor belt of a production line moving with typical speed of about 200 to about 400 m/min (i.e. about 3 to 6 m/s), it is clearly not possible to acquire a luminescent intensity profile I(t), even is the luminescent material has quite a long decay time value of a few ms or more. Thus, identification/authentication of said moving marking is not possible in-line: for example, authenticating a luminescent marking such as a barcode or a datamatrix on an item transported on a conveyor belt. Consequently, in-line secure track and trace operations based on such in-line determination of a luminescent intensity profile are not possible, although highly desirable.

SUMMARY OF THE INVENTION

The present invention is aimed at providing a scanner, and a method for determining an intensity profile of a luminescence emission light from a luminescent material, and a decay time of said luminescent material that overcome the above mentioned drawbacks of the prior art.

The invention also relates to a system for the in-line identification/authentication of an item marked with a luminescent material and transported on a distribution/production line, possibly at high speed, on the basis of decay time characteristics of this material, by using the specific scanner and the decay time detection method according to the invention.

Thus, the invention allows in-line operations of identification/authentication of an item marked with a luminescent material, based on the determination, from a measured intensity profile, of the decay time value of said material or, in case of a material including a mixture of luminescent particles having distinct decay time characteristics, of the decay time values and concentrations corresponding to each type of particles in the mixture.

According to one aspect of the invention, a scanner for determining an intensity profile of luminescence light from a luminescent material moving past said scanner along a path in a first direction, said luminescent material emitting said luminescence light within a second wavelength range upon illumination with an excitation light within a first wavelength range, comprises:

a power source;

a light source connected to the power source and operable to illuminate with said excitation light the luminescent material within an illumination area, when powered by the power source;

a light sensor operable to measure an intensity of said luminescence light received from the luminescent material within a detection zone of said scanner, and deliver a corresponding luminescence intensity signal; and a control unit connected to the light sensor and operable to determine an intensity profile of said received luminescence light, from luminescence intensity signals delivered by the light sensor, wherein:

said illumination area is at a first location along said path;

said detection zone is at a subsequent second location along said path in the first direction, and extends along a portion of said path;

said light sensor is operable to collect luminescence light from the luminescent material during its motion along the path in the first direction across the detection zone, and measure an intensity of said collected luminescence light within said second wavelength range, and deliver a corresponding luminescence intensity signal; and said control unit is operable to control said power source, light source and light sensor, and determine said intensity profile from the luminescence intensity signal delivered by said light sensor upon reception of luminescence light emitted by said luminescent material moving across said detection zone in the first direction, in response to illumination with said excitation light within said illumination area.

The light source may be equipped with an optical filter for delivering the excitation light within the selected first wavelength range. Also, the light sensor may be equipped with an optical filter adapted to receive only the luminescence light which is within the second wavelength range. The respective first and second locations of the illumination zone and the detection zone may be separated or may overlap. This latter compact arrangement being more convenient in case of a luminescent material having a short decay time value and/or a slow motion of said material past the scanner.

The above specific detection zone extending along a path in the direction of motion (i.e. along a trajectory) of the luminescent material, together with the light sensor being specifically adapted to collect luminescent light emitted while the luminescent material is crossing this elongated detection zone, in fact allows the scanner to "follow" said emitting material over a much greater period compared to a scanner of the prior art, even if the luminescent material moves quite fast past the scanner. Indeed, the typical length L of the detection zone along the direction of motion, for a given typical velocity V of the luminescent material running across said detection zone (for example, a mean velocity), may be determined so that the corresponding measuring time interval it of the emitted luminescent intensity is sufficient to acquire a luminescent intensity profile I(t): for example, with $L \geq \Delta t$.

The above scanner according to the invention may further have its light sensor adapted so that the responsivity (i.e. the ratio of generated photocurrent, or output voltage, to incident optical power), within the second wavelength range (i.e. the luminescence emission range of the luminescent material considered), of said light sensor is substantially uniform over the detection zone. Substantially uniform means that the responsivity of the light sensor to a luminescence emission received from a part of the detection zone is constant or only fluctuates around a mean value, for example, by no more than 10%, and preferably no more than 5%, in function of the location of that part within the detection zone. This substantial uniformity of the light sensor responsivity over the detection zone allows eliminating from the measured intensity profile I(t) contributions corresponding to a degraded quantum efficiency of the light sensor for the detection of photons received from a certain region of the detection zone with respect to photons received from another region of the detection zone. As a consequence, the acquired intensity profile shows a variation of intensity over time which is practically only due to the radiative de-excitation of the luminescent particles with time in the luminescent material. Reliability of the determined intensity profile is thus increased. Consequently, it is also possible to obtain a more reliable value of the decay time from such intensity profile. Ideally, the responsivity should be close to the highest possible value for the luminescence wavelength range considered, but still in the linear response range of the light sensor, in order to have a high signal-to-noise ratio value and high sensitivity for the measurements. Spacial uniformity of the responsivity of the light sensor over the detection zone has the further advantage of allowing very high reliable sampling rates for the acquisition of the intensity profile, so that the acquired profile I(t) better approaches a "continuous" curve. Such a better intensity profile curve allows more reliable interpolation, for example in view of accurate derivation or integration operations based on this curve: this being particularly useful in case of complex luminescence signatures from a mixture of different types of luminescent particles, to extract accurate concentration values and decay time values of the constituents of the luminescent material.

The control unit of the scanner may be further adapted to control that responsivity of the light sensor is indeed substantially uniform over the detection zone, i.e. is comprised between authorized limits around an authorized mean value.

A light sensor of a scanner according to the invention may have different configurations corresponding to the above mentioned elongated detection zone and/or substantially uniform responsivity over said detection zone.

The above scanner according to the invention may thus have:

said light sensor comprising a plurality of photodetectors disposed successively along said first direction, each photodetector being operable to measure an intensity of luminescence light received from a corresponding detection area within the detection zone, within the second wavelength range, and deliver a corresponding photodetector luminescence intensity signal, the set of the corresponding detection areas covering said detection zone; and said control unit being operable to determine said intensity profile from the luminescence intensity signals delivered by said photodetectors upon reception of luminescence light emitted by said luminescent material moving across said detection areas along said path in the first direction.

By contrast with a possible case of a "monoblock" light sensor having, for example, a monoblock CCD array for detecting the collected photons, the above configuration of the light sensor corresponds to distinct photodetectors being spaced so as to collect luminescence photons from the detection zone and connected to a circuitry so that the light sensor can measure light intensity from a luminescent material moving through the whole detection zone. These photodetectors may be photodiodes connected in parallel, for example. Moreover, any two successive photodetectors of said plurality of photodetectors may be disposed to have their respective detection areas partially overlapping so that a responsivity of the light sensor within said second wavelength range is substantially uniform over said detection zone.

In another configuration of the above scanner according to the invention, the light sensor may comprise a plurality of optical waveguides, each waveguide having an entry operable to collect luminescence light within said second wavelength range from a corresponding detection area within said detection zone, the plurality of waveguide entries being disposed successively along said first direction and the set of the corresponding detection areas covering said detection zone. For example, said optical waveguides may be optical fibers. Moreover, said optical waveguides may be disposed to have their respective detection areas partially overlapping so that a responsivity of the light sensor within said second wavelength range is substantially uniform over said detection zone. This configuration may correspond, for example, to a light sensor having a compact CCD sensor array for the capture of photons, by contrast with a light sensor having a monoblock CCD sensor array extended, for example, over the whole length of the detection zone so as to directly collect light from it. For example, in case of optical waveguides being optical fibers for collecting luminescence light from an item marked with a luminescent material which is transported on a conveyor belt, entries of these optical fibers are spaced (between them along the direction of motion and at a distance above the luminescent marking), and so that their acceptance cones (or numerical apertures) delimit said partially overlapping areas within the detection zone.

The light sensor may further comprise a focalization device operable to focalize luminescence light received from the detection zone. This may help reducing a constraint on the acceptance cones of the entries of waveguides, for example. Also, the light source may comprise focalization means operable to focalize excitation light on said illumination area. Particularly, said focalization means may focalize excitation light produced by a plurality of LEDs producing the excitation light within the first wavelength range. This configuration of the light source allows providing high excitation light intensity to the luminescent material to better "charge" it, and is also convenient for pulsed light sources.

According to the invention, any of the above scanners may further comprise:

a trigger unit operable to detect that the luminescent material is within the illumination area of the light source, and deliver a corresponding trigger signal; and the control unit is further operable to control the light source to deliver excitation light pulse to the luminescent material within the illumination area upon reception of said trigger signal from the trigger unit, and control the light sensor to acquire the intensity profile after illumination has stopped.

This configuration allows precisely synchronizing motion of the luminescent material across the illumination area of the light source and the detection zone with luminescence intensity profile acquisition operations, i.e. illumination with the light source only while the luminescent material is within the illumination area, followed by measurement of luminescence intensity with the light sensor after illumination has stopped, while the luminescent material crosses the detection zone of the scanner. A scanner having its light sensor comprising a plurality of photodetectors, as described above, may further be adapted to synchronize motion of the luminescent material through the detection zone with measurement operations of the luminescent intensity so that intensity values $I(t_1), \ldots, I(t_n)$ are acquired only while the luminescent material is at specific locations within the detection zone. For example, when the luminescent material is positioned with respect to a photodetector so that irradiance of this photodetector is maximum. Consequently, successive values $I((t_i)$ of the acquired intensity profile correspond to consecutive positions of the luminescent material at which the response from the corresponding photodetector subject to said maximum irradiance is best reliable. Moreover, the control unit may further only select the response of this very photodetector subject to a maximum irradiance as constituting the intensity signal measured by the light sensor when the luminescent material is at the corresponding location in the detection zone.

Thus, the invention also relates to a scanner having its light sensor comprising a plurality of photodetectors, as described above, wherein the scanner further comprises a position sensor operable to determine a position of the luminescent material within said detection zone and deliver a corresponding position signal;

the control unit is further operable to receive a position signal from said position sensor and determine said intensity profile only from consecutive luminescence intensity signals corresponding to consecutive positions of the luminescent material within each of the successive detection areas at which irradiance of the light sensor is maximum.

According to the invention, in order to better detect a difference between intensity profiles of luminescent materials including mixtures of different types of luminescent particles (i.e. having different decay time characteristics), any of the above scanners may further have its power source operable to deliver a variable drive current, or drive voltage to the light source so as to obtain more reliable luminescence intensity signals. Thus, according to the invention, setting the intensity of the excitation light by means of the drive current intensity, or the value of the drive voltage (depending on power supply adapted to the light source), so that the detected luminescence signal is acceptable (i.e. is within the range of reliable operation of the light sensor), allows both obtaining more reliable luminescence intensities and having the same excitation time for each luminescence intensity profile. The luminescence intensity value may be judged acceptable by the control unit if it is within a given range of luminescence intensity values.

For example, in the above mentioned case of two distinct mixtures of luminescent pigments P1 and P2, changing the flux of excitation light for a same excitation time (i.e. changing only the respective illumination intensities at t.sub.0 for the decay curve of P1 and for the decay curve of P2) allows discriminating, or better discriminating, between the different concentrations directly on the normalized profiles for these mixtures. This is illustrated on FIGS. 2A and 2B. FIG. 2A shows a luminescence intensity profile for the above mentioned mixture of 50% of pigments P1 and 50% of pigments P2, for a constant excitation time interval of 100 μs. FIG. 2A is in fact identical to FIG. 1A. FIG. 2B shows a luminescence intensity profile for the above mentioned mixture of 42% of pigments P1 and 58% of pigments P2, for the same constant excitation time interval of 100 μs, but intensity of the illuminating excitation light has been changed compared with the case of FIG. 2A. A difference between the normalized decay curves in FIG. 2A and FIG. 2B is now clearly visible: for example, the intersection point between the normalized intensity profile (P1+P2) and the horizontal line corresponding to the ordinate value of 0.2 has an abscissa value of about 280 μs on FIG. 2B and only about 250 μs on FIG. 2A. Thus, varying the excitation light intensity clearly allows discriminating mixtures of luminescent particles, even if these particles have widely differing decay times. Accordingly, the invention relates to a scanner wherein:

said power source is further operable to deliver a variable drive current or drive voltage;

said light source is further operable to produce said excitation light with an intensity varying according to the delivered drive current or drive voltage; and said control unit is further operable to control said power source to set a value of the drive current, or a value of the drive voltage, delivered to the light source so that a luminescence intensity value corresponding to a delivered luminescence intensity signal is within a given range of luminescence intensity values.

For example, the luminescence intensity value may be above a detection threshold of the light sensor, and below a saturation threshold of the light sensor, i.e. within a reliable detection range of the light sensor. The range of luminescence intensity values may also ensure that a signal to noise ratio of measured luminescence intensity is above a threshold value and/or the light sensor does not saturate during corresponding measurement operation. For example, depending on the measured level of luminescence intensity detected by the light sensor at the end of the illumination cycle, the control unit may adapt the intensity level of the excitation light delivered by the light source, by varying the drive current (or drive voltage) delivered by the power source, so that a luminescence intensity signal delivered at the beginning of the intensity measurement cycle (i.e. just after the end of illumination by the light source) corresponds to an intensity value close to the saturation level of the light sensor, but still below said saturation level: in this case, the measured values are highly reliable and data extracted from the intensity profile are more accurate.

Moreover, the light sensor may further have its detection threshold and saturation threshold adjustable, and the control unit may further be operable to adjust a value of these thresholds. This is particularly interesting for detecting with the light sensor an offset value of an intensity signal corresponding to illumination of the luminescent material only with an ambient light (i.e. without illumination by means of the light source) to be subtracted from the intensity signals constituting the intensity profile, for eliminating any perturbation corresponding to said ambient light: in case the offset value is out of the detection range of the light sensor, the control unit may further adjust the detection range so that the offset value is within the modified detection range. Consequently, the values of luminescence intensity to be measured by the light sensor (to constitute the luminescence intensity profile) in presence of said ambient light will lie within said modified detection range then adapted to the specific actual conditions of measurement, even if the luminescence level is low, and the resulting luminescence intensity profile will be more reliable.

According to the invention, the light source may further be operable to deliver light over an adjustable excitation time interval, and the control unit may further be operable to control said light source to set the excitation time interval. Thus, in case the intensity of the drive current (or drive voltage) of the light source is at its maximum, it is nevertheless possible to still increase the charge of the luminescent material by increasing the excitation time.

Also, in the scanner according to the invention, the control unit may further be operable to control the light sensor to measure an intensity of the luminescence light with a time delay after the excitation time interval has elapsed. Moreover, the control unit may further be operable to set said time delay. Thus, it is possible to better discriminate luminescent materials having very different decay time characteristics. If necessary, the excitation time interval and/or the time delay after the end of illumination may thus be further set to achieve the above goal of obtaining a luminescence intensity value at the beginning of the intensity measurement cycle being close to the saturation level.

The invention further relates to a scanner as described above, wherein said control unit is further operable to determine a decay time value of the luminescent material from said determined intensity profile. Many techniques are known to the skilled person for calculating a decay time value from an intensity profile.

Any one of the above scanners according to the invention may have its control unit further operable to authenticate said luminescent material in case the determined intensity profile I(t) of the luminescent material corresponds to a given reference luminescence intensity profile $I_{ref}(t)$ stored in a memory of the control unit, said reference luminescence intensity profile being a luminescence intensity profile of a reference luminescent material. Thus, curve shapes are used as authenticating features, rather than mere intensity values of individual measurements.

For example, in order to have an even more reliable comparison of the intensity profiles I(t) and $I_{ref}(t)$, each intensity profile may be first normalized, and the normalized profiles are then compared. This normalization has the effect that the comparison becomes model-free and also largely independent of possible intensity deviations due to aging, alterations or dirtiness of the luminescent material marking considered. For example, both luminescence intensity profiles I(t) and $I_{ref}(t)$ are put to scale, such that the highest values of both profiles coincide: if the respectively resulting normalized profiles $\hat{I}(t)$ and $\hat{I}_{ref}(t)$ match within a given tolerance, then the luminescent material is considered as corresponding to the reference luminescent material (i.e. is genuine).

The invention also relates to a scanner having its control unit operable to determine a decay time value of the luminescent material from the determined intensity profile (see above), wherein said control unit is further operable to authenticate said luminescent material in case the decay time value of the luminescent material determined from said intensity profile corresponds to a given reference decay time value stored in a memory of the control unit, said reference decay time value corresponding to a decay time value of a reference luminescent material. For example, the control unit may test if these decay time values match, within a given margin of error: in case of matching, the luminescent material is considered as being genuine. The authentication operation may, in addition to the comparison of determined and reference decay time values, further comprise a comparison of the measured I(t) and reference $I_{ref}(t)$ intensity profiles (the latter being also stored in the memory of the control unit), and/or a comparison of an additional characteristic extracted from these intensity profile curves, such as respective concentrations in luminescent particles within the luminescent material and the reference luminescent material, as known in the art.

Another aspect of the invention relates to a method for determining an intensity profile of luminescence light from a luminescent material moving past a scanner according to the invention along a path in a first direction, said luminescent material emitting said luminescence light within a second wavelength range upon illumination with an excitation light within a first wavelength range, said method comprising the steps of:

illuminating the luminescent material moving past the scanner in the first direction, as it crosses the illumination area of the scanner, with an excitation light within the first wavelength range by means of the light source of the scanner;

as the luminescent material, after having been illuminated with the excitation light, still moves in the first direction and enters the detection zone of said scanner, measuring an intensity of luminescence light emitted by said luminescent material within the second wavelength range while it crosses the detection zone by means of said light sensor, and delivering a corresponding luminescence intensity signal to the control unit of the scanner;

determining an intensity profile from the luminescence intensity signal received by the control unit.

The invention also relates to a method for determining an intensity profile and detecting a decay time of luminescence light from a luminescent material moving past a scanner according to the invention (as described above) along a path in a first direction, said luminescent material emitting said luminescence light within a second wavelength range upon illumination with an excitation light within a first wavelength range, said method comprising the steps of:

illuminating the luminescent material moving past the scanner in the first direction, as it crosses the illumination area of the scanner, with an excitation light within the first wavelength range by means of the light source of the scanner;

as the luminescent material, after having been illuminated with the excitation light, still moves in the first direction and enters the detection zone of said scanner, measuring an intensity of luminescence light emitted by said luminescent material within the second wavelength range while it crosses the detection zone by means of said light sensor, and delivering a corresponding luminescence intensity signal to the control unit of the scanner;

determining an intensity profile from the luminescence intensity signal received by the control unit; and determining a decay time value of the luminescent material from said determined intensity profile.

The control unit of the scanner may be programmed so as to execute the above steps of the method according to the invention. The above method may further comprise a step on controlling that a responsivity of the light sensor within the second wavelength range is substantially uniform over the detection zone of the scanner. For example, the control unit may further control that the light sensor responsivity is comprised between authorized limits around an authorized mean value. In case of a scanner according to the invention which comprises a power source operable to deliver a variable drive current or drive voltage to the light source, as mentioned above, the method according to the invention may further comprise the steps of:

(a) setting a value of the drive current, or a value of the drive voltage, delivered by the power source;

(b) illuminating the luminescent material during said excitation time interval with the light source powered with said value of drive current or drive voltage;

(c) measuring a corresponding value of the intensity of the luminescence light from the luminescent material with the light sensor after said excitation time interval;

(d) judging whether said measured value of the intensity of the luminescence light is acceptable, i.e. is within a given range of luminescence intensity values, and if it is acceptable, (e) storing the measured value in a memory of the control unit as a corresponding point of said intensity profile; and (f) performing steps (c) and (e) successively until completion of said intensity profile over the measuring time interval;

or, if it is not acceptable, (g) setting a modified value of the drive current, or a modified value of the drive voltage, delivered by the power source at step (a) and illuminating the luminescent material at step (b) with the light source powered with said modified value of the drive current or drive voltage, and then performing steps (c) to (f); and (h) determining a decay time value from said stored intensity profile.

Setting the intensity of excitation light by means of the drive current or drive voltage (depending on which supply is convenient for the light source), so that the detected luminescence signal is acceptable, allows measuring reliable intensity profiles corresponding to signals obtained in the same illumination conditions (i.e. with the same excitation time). Thus, the above method particularly allows a much better discrimination between luminescent materials including mixtures of luminescent particles having distinct decay time characteristics and which differ only by their respective concentrations in said particles. At step (h), the stored intensity profile may further be normalized and the decay time value is then determined from the normalized intensity profile. This normalization allows better accuracy of the determined decay time values. The above method, with said control unit of the scanner being further operable to adjust a value of said detection threshold and saturation threshold, may also comprise: a preliminary step of acquiring an initial intensity signal from the light sensor, without illuminating the luminescent material with the light source, to obtain a corresponding offset value corresponding to an ambient light; and, in case said initial intensity signal is out of said detection range of the light sensor, modifying the detection range by a step of adjusting said detection threshold value, or said saturation threshold value, so that said initial intensity signal is within the modified detection range; then, at step (c), subtracting said offset value from the luminescence intensity signal delivered by the light sensor to obtain said measured value of the intensity of the luminescence light, and, in case the detection range has been modified, at step (d), using said modified detection range as the detection range of the light sensor. Thus, a possible contribution of an ambient light to luminescence light detected by the light sensor is then removed and the obtained luminescence intensity profile and corresponding decay time value uniquely relate to the luminescent light emitted by the luminescent material. Consequently, accuracy and reliability of measurements are further increased.

In a variant of the method according to the invention, wherein the light source is operable to deliver light over an adjustable excitation time interval, and the control unit is further operable to control the light source to set the excitation time interval, in case at step (d) a measured value of the intensity of the luminescence light is not acceptable and the corresponding value of the drive current, or the corresponding value of the drive voltage, is below a first threshold value, then step (g) includes a preliminary step of decreasing said excitation time interval, or, in case at step (d) a measured value of the luminescence light is not acceptable and the corresponding value of the intensity of the drive current, or the corresponding value of the drive voltage, is above a second threshold value, then step (g) includes a preliminary step of increasing said excitation time interval. Thus, even if the drive current, or the drive voltage, is too low (i.e. below said first threshold value), or too high (i.e. above said second threshold value), it is possible to try to have an acceptable luminescence signal by adjusting the excitation time interval. It is also possible to include a mere preliminary step of setting the excitation light (independently of any condition on the drive current, or the drive voltage, and the measured luminescence signal).

In the above method according to the invention, at step (c), for the first point of the intensity profile corresponding to the value of the drive current, or the value of the drive voltage, set at step (a), said measuring of the intensity of the luminescence light may be carried out with a time delay after said excitation time interval has elapsed. Also, the control unit may further set this time delay.

With a scanner according to the invention having its control unit further operable to authenticate the luminescent material based on a decay time value determined from the emitted luminescence light, the above method for determining an intensity profile may comprise a further step of authenticating said luminescent material in case the decay time value of the luminescent material determined from said intensity profile corresponds to the given reference decay time value stored in the memory of the control unit of the scanner. For example, if the measured decay time value substantially matches the reference decay time value, the item is considered as being genuine.

With a scanner according to the invention having its control unit further operable to authenticate the luminescent material based on a comparison of a determined intensity profile with a reference intensity profile, as described above, the above method according to the invention comprises the further step of:

authenticating said luminescent material in case the decay time value of the luminescent material determined from said intensity profile corresponds to a given reference decay time value stored in a memory of the control unit, said reference decay time value corresponding to a decay time value of a reference luminescent material.

Finally, the invention relates to a system for determining an intensity profile of luminescence light from a luminescent material moving past a scanner according to any of the above variants according to the invention, along a path in a first direction on a production/distribution line, said luminescent material emitting said luminescence light within a second wavelength range upon illumination with an excitation light within a first wavelength range delivered by the light source of said scanner, said scanner being mounted on said production/distribution line, wherein the control unit of said scanner is programmable and includes a program which, when running on said control unit, makes the control unit operable to implement the steps of the above corresponding method for determining an intensity profile according to the invention.

Embodiments of the invention are directed to a scanner for determining an intensity profile of luminescence light from a luminescent material moving along a path in a first direction, the luminescent material emitting the luminescence light within a second wavelength range upon illumination with excitation light within a first wavelength range. The scanner includes a power source; a light source that is connected to the power source and that is operable to illuminate the luminescent material within an illumination area arranged at a first location along the path with the excitation light; a light sensor operable: to collect luminescence light from the luminescent material during its motion along the path in the first direction across a detection zone that is arranged at a second location along the path that is downstream of the first location and that extends along a portion of the path, to measure an intensity of the collected luminescence light within the second wavelength range from the luminescent material within the detection zone, and to deliver a luminescence intensity signal, wherein an intensity profile of the collected luminescence light is determinable from a plurality of luminescence intensity signals delivered by the light sensor. A responsivity of the light sensor within the second wavelength range is substantially uniform over the detection zone, and the intensity profile from the delivered luminescence intensity signal is determinable upon reception of luminescence light emitted by the luminescent material, which is in response to illumination of the luminescent material within the illumination area with the excitation light.

According to embodiments, the light sensor can include a plurality of photodetectors disposed successively along the first direction, each photodetector being operable to measure an intensity of luminescence light within the second wavelength range received from a corresponding detection area within the detection zone, and to deliver a corresponding photodetector luminescence intensity signal, the plurality of corresponding detection areas covering the detection zone. The intensity profile can be determinable from the luminescence intensity signals delivered by the photodetectors upon reception of luminescence light emitted by the luminescent material moving across the detection areas along the path in the first direction. The photodetectors may be photodiodes connected in parallel. Further, any two successive photodetectors of the plurality of photodetectors can be disposed to have their respective detection areas partially overlapping. In this manner, the responsivity of the light sensor within the second wavelength range may be substantially uniform over the detection zone.

In accordance with other embodiments, the light sensor may include a plurality of optical waveguides, each waveguide having an entry operable to collect luminescence light from a corresponding detection area within the detection zone. The plurality of waveguide entries can be disposed successively along the first direction and the plurality of corresponding detection areas covering the detection zone. The optical waveguides can be optical fibers. Further, the optical waveguides may be disposed to have their respective detection areas partially overlapping, so that the responsivity of the light sensor within the second wavelength range is substantially uniform over the detection zone.

In still other embodiments, the light sensor may further include a lens operable to focalize luminescence light from the detection zone.

According to other embodiments of the invention, the light source may include a plurality of LEDs and at least one lens operable to focalize excitation light from the plurality of LEDs on the illumination area.

In embodiments, the light source can be triggerable to deliver at least one excitation light pulse to the luminescent material within the illumination area of the light source, and the light sensor is controllable to acquire the intensity profile after illumination has stopped.

In accordance with still further features, the scanner may also include a position sensor operable to determine a position of the luminescent material within the detection zone and to deliver a corresponding position signal. The intensity profile can be determinable only from consecutive luminescence intensity signals corresponding to consecutive positions of the luminescent material within each of the successive detection areas at which irradiance of the light sensor is maximum.

In other embodiments, the power source may be operable to deliver a variable drive current or drive voltage and the light source may be operable to produce the excitation light with an intensity varying according to the delivered drive current or drive voltage. The power source can be controllable to set a value of the variable drive current or a value of the variable drive voltage deliverable to the light source so that a luminescence intensity value corresponding to the delivered luminescence intensity signal is within a given range of luminescence intensity values. The given range of luminescence intensity values can correspond to a detection range of the light sensor, and the detection range of the light sensor may be a range of luminescence intensity values between a detection threshold value and a saturation threshold value of the light sensor. Further, the given range of luminescence intensity values can be usable in ensuring that a signal to noise ratio of a measured luminescence intensity is above a threshold value.

According to further embodiments of the invention, the light source can be operable to deliver excitation light over an adjustable excitation time interval. The light sensor may be operable to measure an intensity of the collected luminescence light with a time delay after the adjustable excitation time interval has elapsed.

In still other embodiments, a decay time value of the luminescent material may be determinable from the determined intensity profile. The luminescent material can be authenticatable in case the decay time value of the luminescent material determined from the determined intensity profile corresponds to a given reference decay time value. The reference decay time value can correspond to a decay time value of a reference luminescent material.

According to still further embodiments, the luminescent material may be authenticatable in case the determined intensity profile of the luminescent material corresponds to a given reference luminescence intensity profile. The reference luminescence intensity profile can be a luminescence intensity profile of a reference luminescent material.

Embodiments of the invention are directed to a method for determining an intensity profile of luminescence light from a luminescent material moving past a scanner of a type described above along a path in a first direction, the luminescent material emitting the luminescence light within a second wavelength range upon illumination with an excitation light within a first wavelength range. The method includes illuminating the luminescent material moving past the scanner in the first direction, as it crosses the illumination area of the scanner, with an excitation light within the first wavelength range from the light source; moving the luminescent material, after having been illuminated with the excitation light, in the first direction to enter the detection zone; measuring, via the light sensor, an intensity of luminescence light emitted by the luminescent material within the second wavelength range while it crosses the detection zone, delivering a luminescence intensity signal; and determining an intensity profile from the luminescence intensity signal.

In further embodiments, the method can include determining a decay time value of the luminescent material from the determined intensity profile.

Embodiments of the invention are directed to a method for determining an intensity profile of luminescence light from a luminescent material moving past a scanner of a type described above along a path in a first direction, the luminescent material emitting the luminescence light within a second wavelength range upon illumination with an excitation light within a first wavelength range. The method includes illuminating the luminescent material moving past the scanner in the first direction, as it crosses the illumination area of the scanner, with an excitation light within the first wavelength range from the light source; moving the luminescent material, after having been illuminated with the excitation light, in the first direction to enter the detection zone; measuring, via the light sensor, an intensity of luminescence light emitted by the luminescent material within the second wavelength range while it crosses the detection zone, delivering a luminescence intensity signal; determining an intensity profile from the luminescence intensity signal; and authenticating the luminescent material in case the decay time value of the luminescent material determined from the intensity profile corresponds to a given reference decay time value stored in a memory of the control unit, wherein the reference decay time value corresponds to a decay time value of a reference luminescent material.

According to embodiments, the method can further include authenticating the luminescent material in case the determined intensity profile of the luminescent material corresponds to a given reference luminescence intensity profile stored in a memory of the control unit. The reference luminescence intensity profile is a luminescence intensity profile of a reference luminescent material.

Still yet other embodiments of the present invention are directed to a system for determining an intensity profile of luminescence light from a luminescent material moving past the scanner of a type described above along a path in a first direction on a production/distribution line. The luminescent material can emit the luminescence light within the second wavelength range upon illumination with an excitation light delivered by the light source within the first wavelength range, and the scanner can be mounted on the production/distribution line.

The present invention will be described more fully hereinafter with reference to the accompanying drawings in which like numerals represent like elements throughout the different figures, and in which prominent aspects and features of the invention are illustrated.

BRIEF DESCRIPTION OF THE DRAWINGS

FIG. 3 is a schematic illustration of an optical block of a scanner according to the invention.

DETAILED DESCRIPTION

Figure 1A:
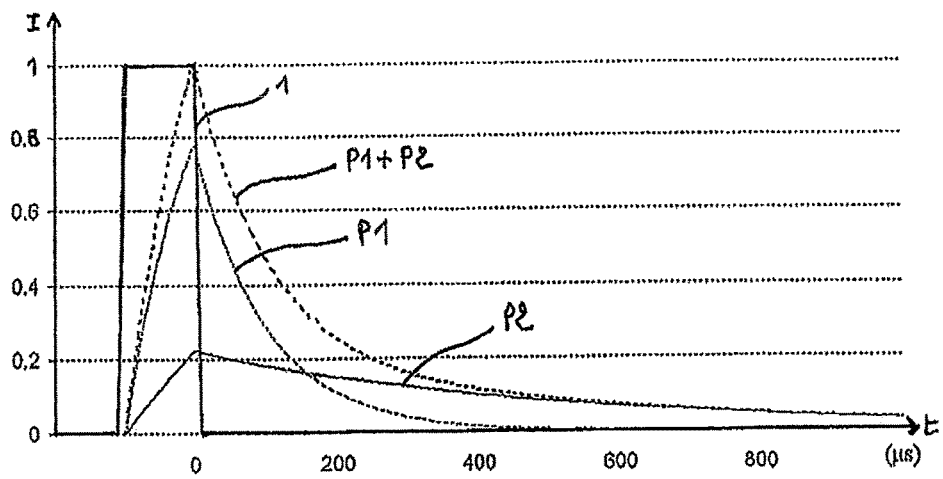
FIG. 1A-1B respectively show normalized decay curves from a conventional scanner with excitation time setting, and light excitation curves, for two luminescent materials corresponding to mixtures of different concentrations in luminescent ink pigments P1 and P2 having distinct decay time characteristics.
Figure 1B:
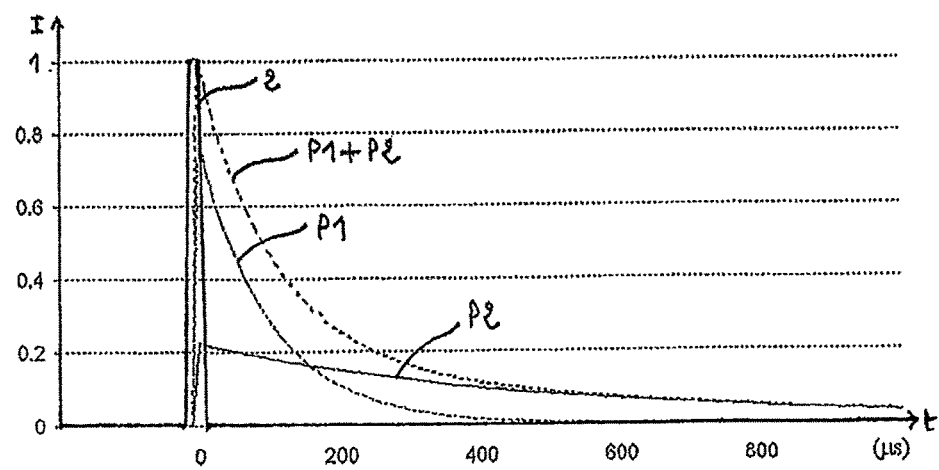
Figure 2A:
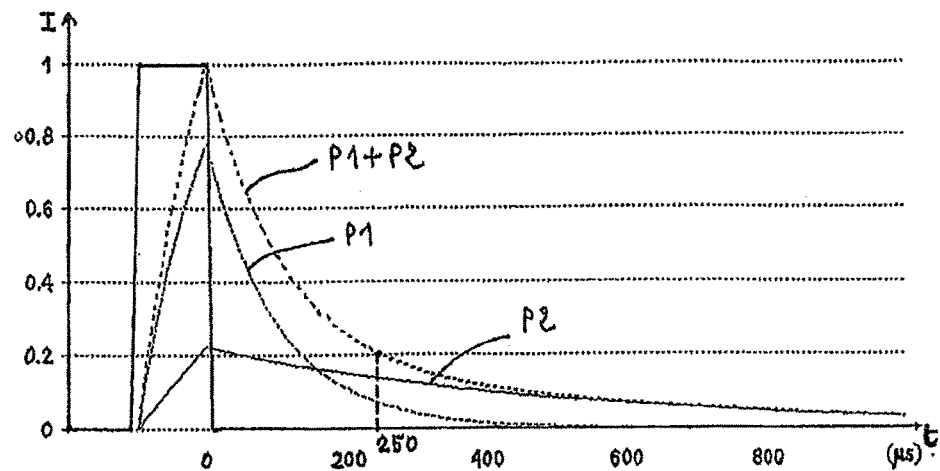
FIG. 2A-2B respectively show normalized decay curves from a scanner according to the invention, with constant excitation time by intensity profile, and light excitation curves, for the two luminescent materials corresponding to the same mixtures as for FIGS. 1A and 1B.
Figure 2B:
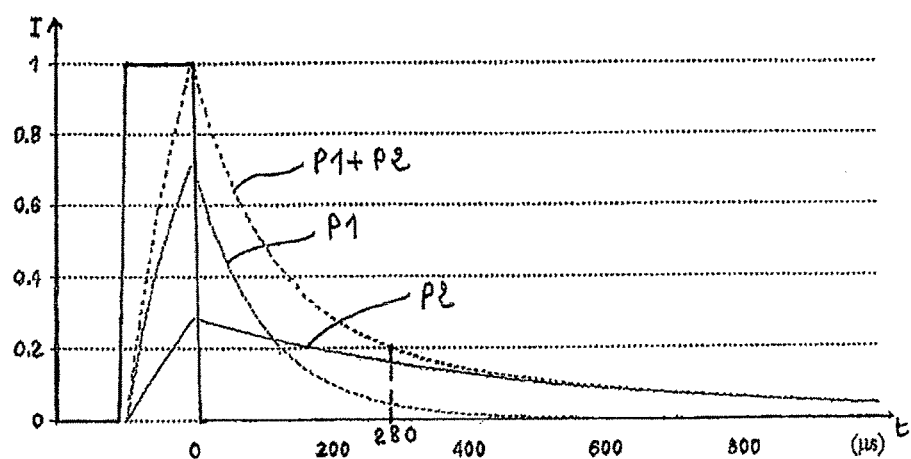

Operation of a scanner for detecting decay time characteristics of a luminescent material according to an example of an embodiment of the invention is illustrated with FIG. 3-9. The scanner (1) is mounted on a production line: items marked with a luminescent material (7) emitting in the near infrared (NIR), when excited with light within a shorter wavelength range (i.e. said first wavelength range), are transported on a conveyor belt (2) of the production line at a typical speed V through the illumination area and the detection zone of the scanner. As an example, this speed may be V≈6 ms$^{-1}$.

The optical block of the scanner (1) (see also FIG. 3) comprises a light source (3) and a light sensor (5). The light source (3) may be, for example, a LED operating with a wavelength at peak emission $\lambda_p$ within the first wavelength range, for a centroid wavelength $\lambda_c$ and a spectral bandwidth at 50% of the maximal drive current intensity $\Delta\lambda$=45 nm (this corresponds to the above mentioned first wavelength range). This LED is operable to produce the excitation light with an intensity varying according to a drive current intensity $I_s$ to illuminate the marking on the item, i.e. the luminescent material (7). The light source is disposed above the conveyor belt (2) and has an illumination cone (17) delimiting an illumination area (8) at a surface of said conveyor belt. The light sensor (5) collects luminescence light emitted by the marking (7) within the detection zone (10) of the scanner (1) by means of photosensors aligned along a direction of motion of the sample (7), above the conveyor belt (2). Here, the light sensor (5) comprises five identical photosensors which are photodiodes PD1 to PD5, each equipped with a focalization lens (18), operable to detect luminescence light in a second wavelength range (in the NIR range). These photodiodes are connected in parallel. The photodiodes are disposed at a distance d 6 mm from each other and at a height h≈15 mm above the conveyor belt (2), as illustrated on FIG. 3. Each photodiode has a detection cone of angle β, here β≈20°, which delimits a corresponding detection area (9) on the conveyor belt (2), within the detection zone (10). The detection areas of any two nearest photodiodes are overlapping, and the union of the five detection areas of the photodiodes in fact constitutes the detection zone (10) of the scanner.

The scanner (1) also comprises a power source (4), for delivering the variable drive current intensity $I_s$ to the light source (3), and a control unit (6) operable to control the power source (4), the light source (3) and the light sensor (5) so as to acquire an intensity profile I(t) of the luminescence light emitted by the marking (7), from luminescence intensity signals delivered over a measuring time interval $\Delta t_m$ by the light sensor (5), and determine a decay time value from the acquired intensity profile I(t). The control unit (6) also receives the luminescence intensity signals from the light sensor (5) and controls the power source (4) to select an intensity value of the drive current $I_s$ delivered to the light source (3) so that a luminescence intensity value $I_L$ corresponding to a delivered luminescence intensity signal is both above the detection threshold of the light sensor (5) and below its saturation level (i.e. in its reliability range).

Figure 4:
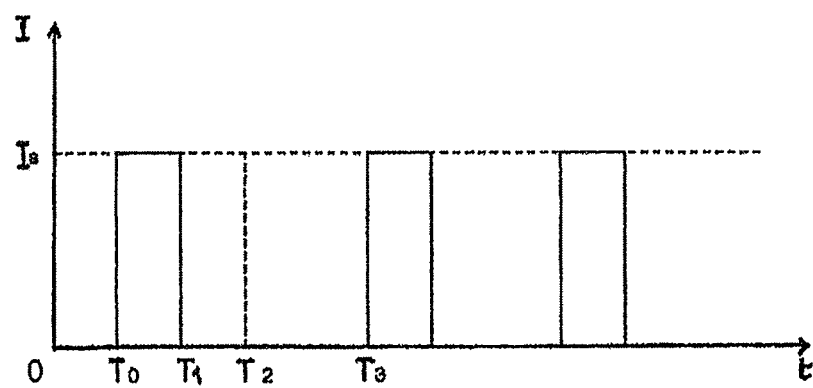
FIG. 4 illustrates an illumination cycle of a light source of the scanner of FIG. 3.

FIG. 4 illustrates an illumination cycle of the light source (3): the light source is powered with drive current intensity $I_s$ between instants $T_0$ and $T_1$. The excitation time interval being $\Delta t_{ex}=T_1-T_0$: here, $\Delta t_{ex}$=100 μs. For the light sensor (5), a time delay $\Delta t_d$ corresponding to $(T_2-T_1)$ can be set by the control unit, and at T.sub.3 a new cycle starts, here $T_3-T_1$=4 ms. The measuring time interval $\Delta t_m$ of the light sensor thus corresponds to $(T_3-T_2)$.

Figure 5:
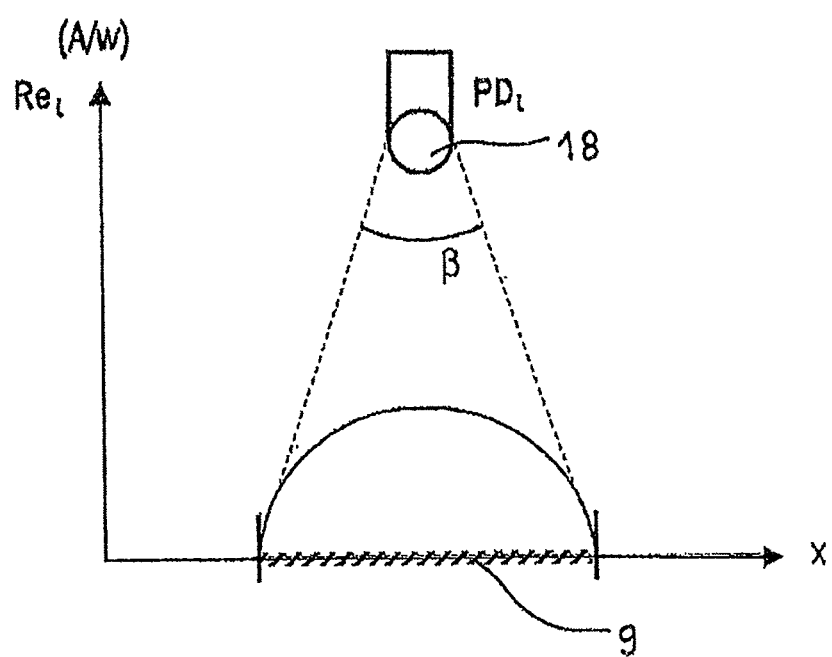
FIG. 5 illustrates a responsivity curve of one of the photosensors in the light sensor of the scanner of FIG. 3.

FIG. 5 illustrates a typical responsivity (within the second wavelength range) of any one of the five photodiodes, say PDi, equipped with its focalization lens (18), as a function $Re_i(x)$ of a position x of a light emitting sample within the detection area (9) of the photodiode, along the direction of motion of the marking (7). The responsivity (in A/W) goes to zero near the boundary of the detection area (corresponding to hatched region), and reaches a maximum at the center of the detection area.

Figure 6:
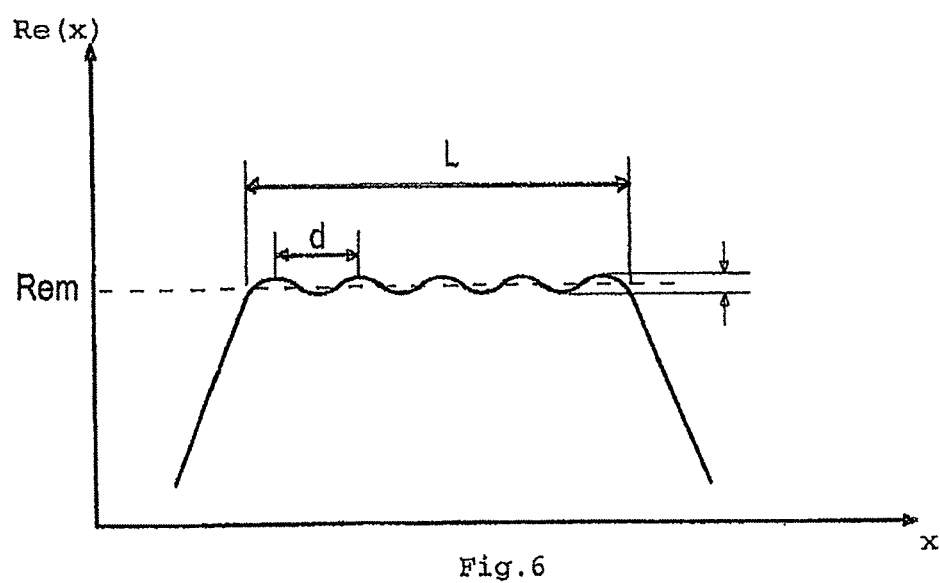
FIG. 6 illustrates a responsivity curve of the light sensor of the scanner of FIG. 3.

FIG. 6 illustrates the responsivity Re(x) of the light sensor (5), within the second wavelength range, as a function of a position x of a light emitting sample within the detection zone (10) of the photodiode. The distance d between the photodiodes and the height h of the photodiodes above the conveyor belt are adapted so that the overall responsivity Re(x) of the light sensor, due to the resulting overlapping of the detection areas (the angle β being given), in fact is substantially uniform through the detection zone (10). Here, the overall responsivity Re(x) of the light sensor (5), as a function of position x within the detection zone (10) of the scanner, along the direction of motion of the sample (7), only fluctuates by less than 5% around a mean value Rem over a uniformity length L, and fall down to zero at the boundary of the detection zone (i.e. on either side of the uniformity region of length L). Here, Rem≈0.6 A W$^{-1}$. The distance d between the photodiodes and height h of the photodiodes above the conveyor belt are set to have both L V $\Delta t_m$ and an overlapping of the detection areas (9) sufficient to obtain said substantial uniformity of the responsivity Re(x) of the light sensor over the length L. Here, we have: L≈5 d≈30 mm. The combination of the detection zone (10) elongated along the direction of motion of the marking (7) and the substantial uniformity of the responsivity of the light sensor over a length L within the detection zone, allows measuring the luminescence light from the marking as it crosses the region of length L in conditions which are quite similar to those of an ordinary scanner being disposed stationary above said marking and following it during its motion through said region. Thus, motion of the marking is "compensated" due to the specific structure of the scanner, even if the marking is moving fast through the detection zone.

Figure 7:
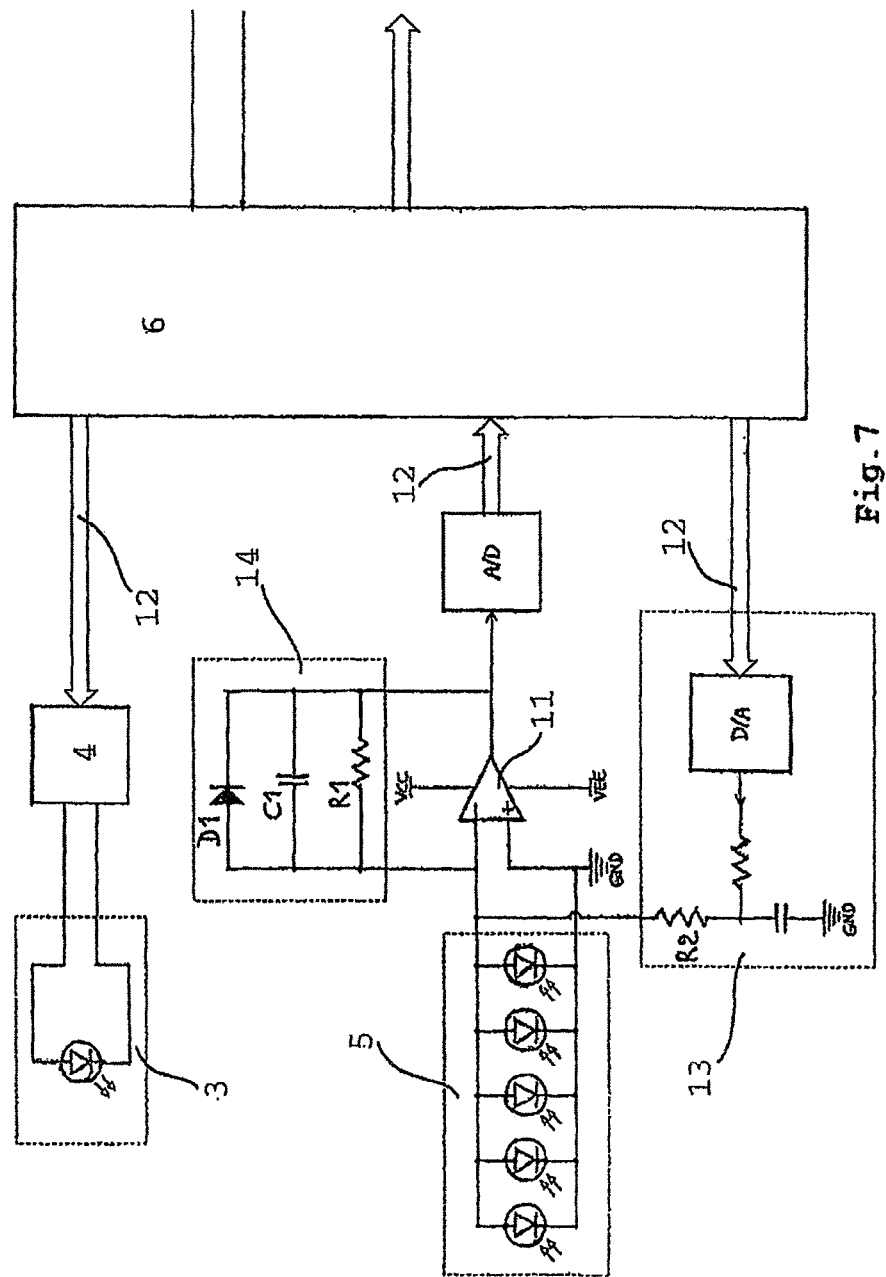
FIG. 7 illustrates an electrical circuit scheme of a scanner according to the invention.

FIG. 7 illustrates a circuit scheme relating to a preferred embodiment of a scanner according to the invention: the control unit (6), via a data bus (12) and a D/A converter (not represented), controls the power source (4), i.e. sets the drive current intensity $I_S$ to power the light source (3), and the values $T_0$ and $T_1$ of the illumination cycle (so as to have the desired values of $\Delta t_{ex}$). The control unit (6) further controls the light sensor (5) via the data bus (12) and a D/A converter of an ambient light offset compensation unit (13), i.e. sets the values $T_2$ and $T_3$ of the measurement cycle (so as to have the desired values of $\Delta t_d$ and $\Delta t_m$). An operational amplifier (11) connected to the light sensor (5) delivers a voltage signal corresponding to a luminescence intensity signal measured by the light sensor (5), via an A/D converter connected to the data bus (12), to the control unit (6).

In order to ensure fast return to unsaturated state of the photodiodes of the light sensor (5), said light sensor in fact acts as a current source (under illumination by luminescence light from the sample) and is always shortened, thus preventing the internal capacities of the photodiodes of being charged and making the response of the photodiodes faster.

Indeed, a diode D1 connected in parallel with a capacitor C1 and a resistor R1, lets current flow in case of a too high voltage at the output of the operational amplifier (11), thus preventing saturation of the operational amplifier. The diode D1 is thus disposed in the negative feedback loop of the operational amplifier (11), which allows the photodiodes of the light sensor (5) being always shortened, and thus never saturated. Consequently, it is possible to acquire an intensity profile much faster and measure shorter decay times. Also, a resistor R2, connected directly at the output of the photodiodes (5), absorbs the offset current so as to shift down a relevant part of the measured intensity signal within a reliable detection range of the A/D converter which sends the measured intensity signal to the control unit (6) through the data bus (12). The part of the intensity signal which is due to ambient light is thus suppressed at the output of the photodiodes (5), and only intensity signals of which offset current has been removed are sent from the operational amplifier (11) to the control unit (6), via an A/D converter and through the data bus (12), to form an accurate intensity profile I(t). Moreover, linearity of the response to luminescence light is increased due to the fact that the photodiodes (5) operate as a current generator and the diode D1, in the negative feedback loop of the operational amplifier (11), always works around the same operating point.

Controlling intensity of the excitation light emitted by the LED (3) by means of its drive current intensity $I_s$, according to this embodiment of the invention, presents the advantage of producing well controlled light flashes, both in duration and intensity shape. This method is efficient, as in most cases an acceptable value of $I_s$, for accurately determining the first point of the luminescence intensity profile, is obtained with only three flashes (see step (g) of the above explained method).

In a preferred embodiment of the invention, the control unit (6) is further operable to adjust the levels of detection threshold and saturation threshold of the light sensor (5), which constitutes a detection range of the light sensor. Thus, the light sensor sensitivity can be adapted to the actual conditions prevailing during measurement of the luminescence light intensity, and the resulting luminescence intensity profile is more reliable.

Operation of the scanner according to said preferred embodiment of the invention is detailed as follows: in a preliminary phase, an initial intensity signal from the light sensor (5), is acquired without illuminating the luminescent material with the LED (3) and without time delay ($\Delta t_d=0$) (as ambient light usually only fluctuates around a constant value during measurement), and an offset value of light intensity $I_{OFF}$ corresponding to ambient light is then determined. The ambient light intensity being usually quite low, if the initial intensity signal is out of a detection range of the light sensor, the control unit (6) then modifies this detection range by adjusting the detection threshold value, and/or the saturation threshold value of the range, so that the initial intensity signal now lies within the new detection range. Then, operation for illuminating said down-converter luminescent material begins: the control unit (6) sets a value of the intensity of the drive current I.sub.S0 delivered by the power source (4); the light source (3) is then powered with this drive intensity, for an excitation time interval $\Delta t_{ex}=100$ µs, and $\Delta t_d$ now set to 60 µs, and $\Delta t_m=4000$ µs, and illuminates the luminescent material during said 100 µs. The control unit (6) also controls the light sensor (5) to measure a corresponding value of the intensity of the luminescence light then emitted by the luminescent material immediately after the excitation time interval of 100 µs. The light sensor (5) then delivers a first luminescence intensity signal to the control unit (6), which then subtracts the offset value of intensity from the corresponding first measured value of the intensity of the luminescence light and judges if the result is acceptable (i.e. lies within the detection range of the light sensor (5)), and if it is acceptable, the result is stored in a memory of the control unit (6) as a corresponding first point of said intensity profile; and measurements of the decaying luminescence light are then performed during the measuring time interval $\Delta t_m=4000$ is, and the corresponding results obtained as explained above constitutes the measured luminescence intensity profile I(t). Said stored profile is then used by the control unit (6) for calculating a corresponding decay time value (or for comparison with a reference intensity profile).

In case the above mentioned result corresponding to the first measured value of the intensity of the luminescence light does not lie within the detection range (usually, this corresponds to a situation wherein the first luminescence signal is above the saturation threshold of the light sensor), the control unit (6) modifies the value of the intensity of the drive current delivered by the power source to the light source (is the first signal is too high, the drive current intensity is decreased). Then, the cycle of illumination, measurement (with offset correction) and judgement is repeated until a luminescence intensity profile is acquired, and a corresponding decay time value is calculated.

In a variant of the invention, in case the first luminescence signal is above the saturation threshold of the light sensor, a further step of increasing the value of the saturation threshold and then repeating the measurement for the first point is tried, instead of modifying the value of the intensity of the drive current, said drive current being modified only if the further step fails to give an acceptable first point of the intensity profile.

The invention is not strictly limited to the above embodiments and various modifications may be made without departing from the scope of the invention as defined by the claims. For example, the light source used for delivering excitation light may be any conventional one having a drive current setting or, equivalently, a supply voltage setting, so as to allow adapting the excitation light intensity delivered by the light source according to a level of light intensity detected by a light sensor by changing the drive current or the supply voltage of the light source.

The decay time scanner and the decay time detection method according to the invention may be used for any luminescence emission in the spectrum range from UV light (200-400 nm), visible light (400-700 nm) or near to mid infrared light (700-2500 nm). A scanner according to the invention may also comprise a radio module for (possibly, wireless) communication, a display module for displaying measured data or scanning parameters, and a controlling interface for inputting scan conditions.

The invention also relates to a use of the decay time scanner and the intensity profile determination method according to the invention for determining decay time characteristics of a luminescent material and/or authenticating an item comprising a luminescent material on the basis of its decay time characteristics; said decay time characteristics being a luminescence emission intensity profile or a decay time value, or concentrations of different types of luminescent particles in said material in case the luminescent material includes a mixture of said types of particles.

What is claimed:
1. A scanner for determining an intensity profile of luminescence light from a luminescent material moving along a path in a first direction, the luminescent material emitting the luminescence light within a second wavelength range upon illumination with excitation light within a first wavelength range, comprising:
- a power source;
- a light source that is connected to the power source and that is operable to illuminate the luminescent material within an illumination area with the excitation light;
- a light sensor operable:
  - to collect luminescence light from the luminescent material during its motion along the path in the first direction across a detection zone,
  - to measure an intensity of the collected luminescence light within the second wavelength range from the luminescent material within the detection zone, and
  - to deliver a luminescence intensity signal, wherein an intensity profile of the collected luminescence light is determinable from a plurality of luminescence intensity signals delivered by the light sensor,
- wherein said illumination area is at a first location along said path;
- said detection zone is at a second location along said path that is downstream of the first location and that extends along a portion of said path;
- wherein a responsivity of the light sensor within the second wavelength range is substantially uniform over the detection zone, and
- wherein the intensity profile from the delivered luminescence intensity signal is determinable upon reception of luminescence light emitted by the luminescent material, which is in response to illumination of the luminescent material within the illumination area with the excitation light.

2. The scanner according to claim 1, wherein the light sensor comprises a plurality of photodetectors disposed successively along the first direction, each photodetector being operable to measure an intensity of luminescence light within the second wavelength range received from a corresponding detection area within the detection zone, and to deliver a corresponding photodetector luminescence intensity signal, the plurality of corresponding detection areas covering the detection zone; and
  - wherein the intensity profile is determinable from the luminescence intensity signals delivered by the photodetectors upon reception of luminescence light emitted by the luminescent material moving across the detection areas along the path in the first direction.

3. The scanner according to claim 2, wherein the photodetectors are photodiodes connected in parallel.

4. The scanner according to claim 2, wherein any two successive photodetectors of the plurality of photodetectors are disposed to have their respective detection areas partially overlapping, whereby the responsivity of the light sensor within the second wavelength range is substantially uniform over the detection zone.

5. The scanner according to claim 1, wherein the light sensor comprises a plurality of optical waveguides, each waveguide having an entry operable to collect luminescence light from a corresponding detection area within the detection zone, the plurality of waveguide entries being disposed successively along the first direction and the plurality of corresponding detection areas covering the detection zone.

6. The scanner according to claim 5, wherein the optical waveguides are optical fibers.

7. The scanner according to claim 5, wherein the optical waveguides are disposed to have their respective detection areas partially overlapping, whereby the responsivity of the light sensor within the second wavelength range is substantially uniform over the detection zone.

8. The scanner according to claim 1, wherein the light sensor further comprises a lens operable to focalize luminescence light from the detection zone.

9. The scanner according to claim 1, wherein the light source comprises a plurality of LEDs and at least one lens operable to focalize excitation light from the plurality of LEDs on the illumination area.

10. The scanner according to claim 1, wherein the light source is triggerable to deliver at least one excitation light pulse to the luminescent material within the illumination area of the light source, and the light sensor is controllable to acquire the intensity profile after illumination has stopped.

11. The scanner according to claim 2, further comprising a position sensor operable to determine a position of the luminescent material within the detection zone and to deliver a corresponding position signal, wherein the intensity profile is determinable only from consecutive luminescence intensity signals corresponding to consecutive positions of the luminescent material within each of the successive detection areas at which irradiance of the light sensor is maximum.

12. The scanner according to claim 1, wherein the power source is operable to deliver a variable drive current or drive voltage and the light source is operable to produce the excitation light with an intensity varying according to the delivered drive current or drive voltage, wherein the power source is controllable to set a value of the variable drive current or a value of the variable drive voltage deliverable to the light source so that a luminescence intensity value corresponding to the delivered luminescence intensity signal is within a given range of luminescence intensity values.

13. The scanner according to claim 12, wherein the given range of luminescence intensity values corresponds to a detection range of the light sensor, and wherein the detection range of the light sensor is a range of luminescence intensity values between a detection threshold value and a saturation threshold value of the light sensor.

14. The scanner according to claim 12, wherein the given range of luminescence intensity values is usable in ensuring that a signal to noise ratio of a measured luminescence intensity is above a threshold value.

15. The scanner according to claim 1, wherein the light source is operable to deliver excitation light over an adjustable excitation time interval.

16. The scanner according to claim 15, wherein the light sensor is operable to measure an intensity of the collected luminescence light with a time delay after the adjustable excitation time interval has elapsed.

17. The scanner according to claim 1, wherein a decay time value of the luminescent material is determinable from the determined intensity profile.

18. The scanner according to claim 17, wherein the luminescent material is authenticatable in case the decay time value of the luminescent material determined from the determined intensity profile corresponds to a given reference decay time value, wherein the reference decay time value corresponds to a decay time value of a reference luminescent material.

19. The scanner according to claim 1, wherein the luminescent material is authenticatable in case the determined intensity profile of the luminescent material corresponds to a given reference luminescence intensity profile, wherein the reference luminescence intensity profile is a luminescence intensity profile of a reference luminescent material.

20. A method for determining an intensity profile of luminescence light from a luminescent material moving past a scanner according to claim 1 along a path in a first direction, the luminescent material emitting the luminescence light within a second wavelength range upon illumination with an excitation light within a first wavelength range, the method comprising the steps of:
- illuminating the luminescent material moving past the scanner in the first direction, as it crosses the illumination area of the scanner, with an excitation light within the first wavelength range from the light source;
- moving the luminescent material, after having been illuminated with the excitation light, in the first direction to enter the detection zone;
- measuring, via the light sensor, an intensity of luminescence light emitted by the luminescent material within the second wavelength range while it crosses the detection zone, and
- delivering a luminescence intensity signal; and
- determining an intensity profile from the luminescence intensity signal.

21. The method according to claim 20, further comprising determining a decay time value of the luminescent material from the determined intensity profile.

22. A method for determining an intensity profile of luminescence light from a luminescent material moving past a scanner according to claim 18 along a path in a first direction, the luminescent material emitting the luminescence light within a second wavelength range upon illumination with an excitation light within a first wavelength range, the method comprising the steps of:
- illuminating the luminescent material moving past the scanner in the first direction, as it crosses the illumination area of the scanner, with an excitation light within the first wavelength range from the light source;
- moving the luminescent material, after having been illuminated with the excitation light, in the first direction to enter the detection zone;
- measuring, via the light sensor, an intensity of luminescence light emitted by the luminescent material within the second wavelength range while it crosses the detection zone, and
- delivering a luminescence intensity signal;
- determining an intensity profile from the luminescence intensity signal; and
- authenticating the luminescent material in case the decay time value of the luminescent material determined from the intensity profile corresponds to a given reference decay time value stored in a memory of the control unit, wherein the reference decay time value corresponds to a decay time value of a reference luminescent material.

23. The method according to claim 20, further comprising authenticating the luminescent material in case the determined intensity profile of the luminescent material corresponds to a given reference luminescence intensity profile stored in a memory of the control unit, wherein the reference luminescence intensity profile is a luminescence intensity profile of a reference luminescent material.

24. A system for determining an intensity profile of luminescence light from a luminescent material moving past the scanner according to claim 1 along a path in a first direction on a production/distribution line,
- wherein the luminescent material emits the luminescence light within the second wavelength range upon illumination with an excitation light delivered by the light source within the first wavelength range,
- wherein the scanner is mounted on the production/distribution line.

* * * * *